(12) United States Patent
Davenport et al.

(10) Patent No.: US 7,541,577 B2
(45) Date of Patent: Jun. 2, 2009

(54) METHODS FOR ANALYZING ION MOBILITY DATA

(75) Inventors: David Michael Davenport, Niskayuna, NY (US); Thomas Paul Repoff, Sprakers, NY (US); Pierino Gianni Bonanni, Clifton Park, NY (US); Richard Louis Zinser, Niskayuna, NY (US)

(73) Assignees: General Electric Company, Niskayuna, NY (US); GE Homeland Protection, Inc., Newark, CA (US)

( * ) Notice: Subject to any disclaimer, the term of this patent is extended or adjusted under 35 U.S.C. 154(b) by 493 days.

(21) Appl. No.: 11/426,442

(22) Filed: Jun. 26, 2006

(65) Prior Publication Data

US 2008/0067341 A1 Mar. 20, 2008

(51) Int. Cl.
*H01J 49/04* (2006.01)

(52) U.S. Cl. ................. 250/288; 73/863.21; 73/863.33; 73/863.83

(58) Field of Classification Search ................. 250/282, 250/288, 286, 287
See application file for complete search history.

(56) References Cited

U.S. PATENT DOCUMENTS

| | | | |
|---|---|---|---|
| 3,699,333 A | 10/1972 | Cohen et al. | |
| 5,027,643 A | 7/1991 | Jenkins | |
| 5,071,771 A | 12/1991 | Barbour et al. | |
| 5,162,652 A * | 11/1992 | Cohen et al. | 250/288 |
| 5,200,614 A | 4/1993 | Jenkins | |
| 5,405,781 A * | 4/1995 | Davies et al. | 436/52 |
| 5,491,337 A | 2/1996 | Jenkins et al. | |
| 6,495,824 B1 | 12/2002 | Atkinson | |
| 6,572,825 B1 | 6/2003 | Linker et al. | |
| 6,815,670 B2 | 11/2004 | Jenkins et al. | |
| 6,831,273 B2 | 12/2004 | Jenkins et al. | |
| 6,924,477 B2 * | 8/2005 | DeBono et al. | 250/282 |
| 2004/0188604 A1 * | 9/2004 | DeBono et al. | 250/282 |
| 2005/0133716 A1 | 6/2005 | Miller et al. | |
| 2005/0253061 A1 | 11/2005 | Cameron et al. | |
| 2006/0151687 A1 * | 7/2006 | Miller et al. | 250/282 |
| 2007/0228269 A1 * | 10/2007 | Miller et al. | 250/282 |

OTHER PUBLICATIONS

PCT International Search Report dated Jan. 11, 2008.
Liew et al., "Corrosion of Magnetic Recording Heads and Media", Tribology International, vol. 36, pp. 447-454, 2003.
Keller, Thomas, et al.; Ion Mobility Spectrometry for the Detection of Drugs in Cases of Forensic and Criminalistic Relevance; IJIMS 2(1999)1; pp. 22-34.
Payne, Kent, et al.; IMS for Cleaning Verification; The Role of Spectroscopy in Process Analytical Technologies; Jan. 2005; www.spectroscopyonline.com; pp. 24-27.

(Continued)

*Primary Examiner*—Nikita Wells
*Assistant Examiner*—Johnnie L Smith, II
(74) *Attorney, Agent, or Firm*—Scott J. Asmus

(57) ABSTRACT

Disclosed herein are methods for analyzing ion mobility data. In one embodiment, a method for analyzing ion mobility spectrometry data is disclosed. The method comprises conducting a number of ion mobility scans on a sample, generating an ion map comprising a first ion line, comparing the first ion line to a standard deviation, wherein the standard deviation is calculated from the system measurement noise, and determining if the sample is a contraband substance.

31 Claims, 6 Drawing Sheets

OTHER PUBLICATIONS

PCT Written Opinion of the International Searching Authority, Dec. 19, 2007.

Brand, Gerek, et al.; Ion trap mobility spectrometry-reducing downtime in cleaning validation and verification; GE Sensing Technical Paper; Derek.brand@ge.com; 7 pages.

Eiceman, G.A., et al.; Ion Mobility Spectrometers in National Defense; Analytical Chemistry; Nov. 1, 2004; pp. 390 A-397 A.

ITMS Ion Trap Mobility Spectrometry—The Science Behind the Technology; GE Technical Paper; www.geiontrack.com; 6 pages.

* cited by examiner

METHODS FOR ANALYZING ION MOBILITY DATA

BACKGROUND

Ion mobility spectrometers (IMS) are used to detect the presence of molecules of interest in a gas stream. This is achieved by passing a carrier gas comprising a minute concentration of a sample vapor (e.g., about ten parts per million) into a detector. The detector comprises an ionization chamber and a drift chamber. In the ionization chamber the carrier gas and the sample vapor are ionized via an ionization source, such as radioactive materials (e.g., nickel-63 or tritium).

A grid disposed at the end of the ionization chamber is normally maintained at the same potential as the walls of the ionization chamber in order to provide a space in which electrons and ions can accumulate and interact therein. When desired, (e.g., about every 20 milliseconds (ms)) the potential of the ionization chamber can be altered for a relatively short duration (e.g., about 0.10 to about 0.20 ms) to carry a desired amount of the ions from the ionization chamber into the drift chamber.

The drift chamber comprises electrodes that are disposed along its length and a collector (e.g., anode) disposed at an end that is opposite the inlet port from the ionization chamber. The electrodes can produce an electrical field within the chamber (positive or negative based on the specific molecules of interest) that causes the ions to travel from the inlet port towards the collector. Upon contact with the collector, the ion's current is detected as well as the time the ion required to pass through the drift chamber. The data from this analysis can then be compared to a library (e.g., a computer database) of known materials and the ion can be identified.

After the ionization chamber has allowed ample ions to pass into the drift chamber, the potential is reverted to that of an electrical charge free state such that additional ions can accumulate within the ionization chamber in anticipation for another measurement cycle.

IMS's have been employed in many applications for the identification of substances of interest, such as for the identification of narcotics and other contraband. This is achieved by constructing a graph of drift time versus scan index (i.e., a sequential listing of individual scans) called a plasmagram, for the sample substance and comparing the graph to those of known substances in a library (e.g., a database). However, the algorithms employed within the IMS (e.g., algorithms in the form of software, hardware, memory, and so forth) are only capable of accurately identifying substances that exhibit repeatable and linear drift time values with respect to sequential scans. Although many substances exhibit repeatable and linear drift time values, volatile chemical taggants such as those incorporated into explosives, exhibit non-linear and concentration-dependent responses, which can also be referred to as peak shifting. Peak shifting in the plasmagram may be caused by a chemical phenomenon in the detector, such as clustering of ion clouds as compounds migrate down the drift chamber. In other cases, peak shifting occurs as the result of molecular thermal instability of compounds that cause intermediate products to form, wherein the intermediate products are unstable and do not produce refined peaks, but rather a large shift in the drift time peak. There are other phenomena that may occur that are not described here that could also produce peak shifting.

As a result, there is a need in the art for methods for analyzing ion mobility spectrometry data that allows for the detection of molecules that exhibit non-linear and/or concentration dependent responses.

BRIEF SUMMARY

Disclosed herein are methods for analyzing ion mobility data.

In one embodiment, a method for analyzing ion mobility spectrometry data is disclosed. The method comprises conducting a number of ion mobility scans on a sample, generating an ion map comprising a first ion line, comparing the first ion line to a standard deviation, wherein the standard deviation is calculated from the system measurement noise, and determining if the sample is a contraband substance.

In another embodiment, a method for analyzing ion mobility spectrometry data is disclosed. The method comprises, conducting a number (n) of ion mobility scans on a sample, generating a first data array comprising a plurality of scan times, generating a second data array comprising a plurality of drift times (td), identifying an ion line using the first data array and second data array, wherein the ion line comprises a line length, a start point (start) and a stop point (stop), calculating an average drift time (avg.) for the ion line, calculating a non-flatness value (Non-Flatness), and determining if the sample is a contraband substance.

In yet another embodiment, a method for analyzing ion mobility spectrometry data is disclosed. The method comprises; conducting an ion mobility scan on a sample, constructing a composite line set comprising a composite ion line formed by data points, determining if the composite ion line exhibits a variation in drift time that is greater than or equal to a minimum value within a scan time range, and determining if the sample is a contraband substance.

The above described and other features are exemplified by the following figures and detailed description.

BRIEF DESCRIPTION OF THE DRAWINGS

Refer now to the figures, which are exemplary embodiments, and wherein the like elements are numbered alike.

DETAILED DESCRIPTION

Disclosed herein are methods for analyzing ion mobility spectrometry data. To be more specific, methods for analyzing ion mobility spectrometry data are disclosed that are capable of detecting contraband substances that produce non-linear and/or concentration dependent ion drift time responses. In a first method, positive and negative ion lines are analyzed with respect to a standard deviation (calculated from the expected system noise) to determine if the test sample is contraband. In a second method, the non-flatness of the positive and negative ion lines is evaluated to determine if a sample is contraband. In a third method, positive and negative ion lines are used to form a composite line set comprising composite ion lines. The composite ion lines are then compared to know ion lines to determine if the composite ion lines are contraband.

Figure 1:
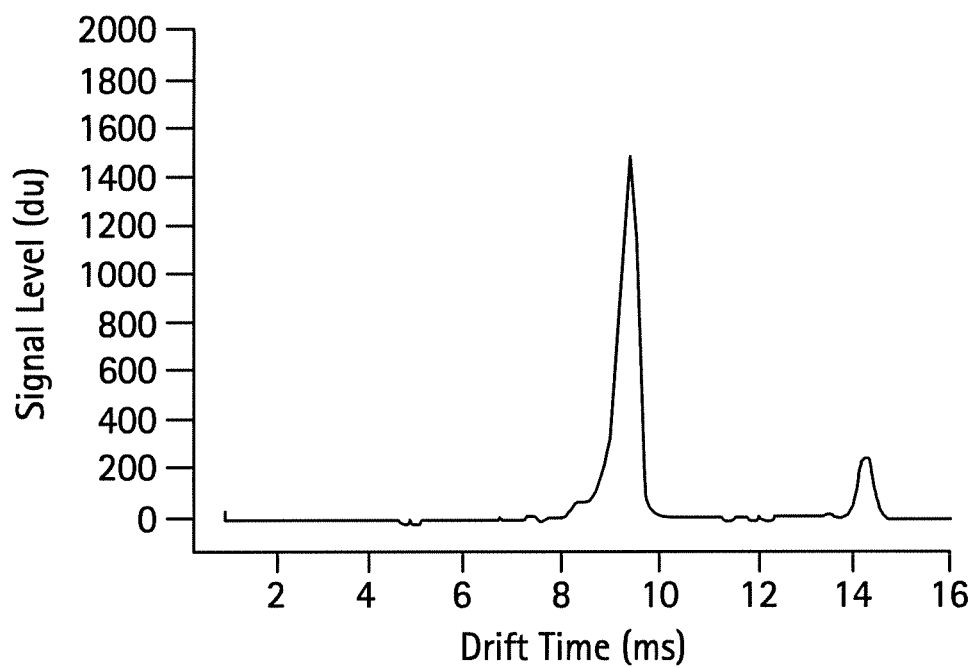
FIG. 1 is a graphical illustration of an exemplary two dimensional (2-D) plasmagram.

IMS's generally measure ion drift time through a drift chamber and the corresponding current measured upon contact of the ion with a collector (e.g., an anode). From these data, a graph (e.g., a 2-D plasmagram) can be generated for either positive or negative ions (based on the test being conducted). Referring now to FIG. 1, an exemplary 2-D plasmagram is illustrated, wherein drift time is disposed on the X-axis and signal level on the Y-axis. As can be observed, drift time is generally presented in milliseconds (ms) and can reach values of about 10 ms or greater, or even 20 ms or greater. Signal level can be presented using any measure of the amplitude or intensity of the signal produced by the IMS. For example, digital units (du) can be employed which are analog to digital converter levels corresponding to voltage (e.g. the output of a 16-bit +/−5V A/D converter). In another example, signal intensity can be presented in millivolts (voltage), milliamps (current), or even in a normalized value or even a percentage. Specifically in FIG. 1, at a drift time of about 9 ms, the plasmagram illustrates a peak having a maximum signal level of about 1,500 du.

Figure 2:
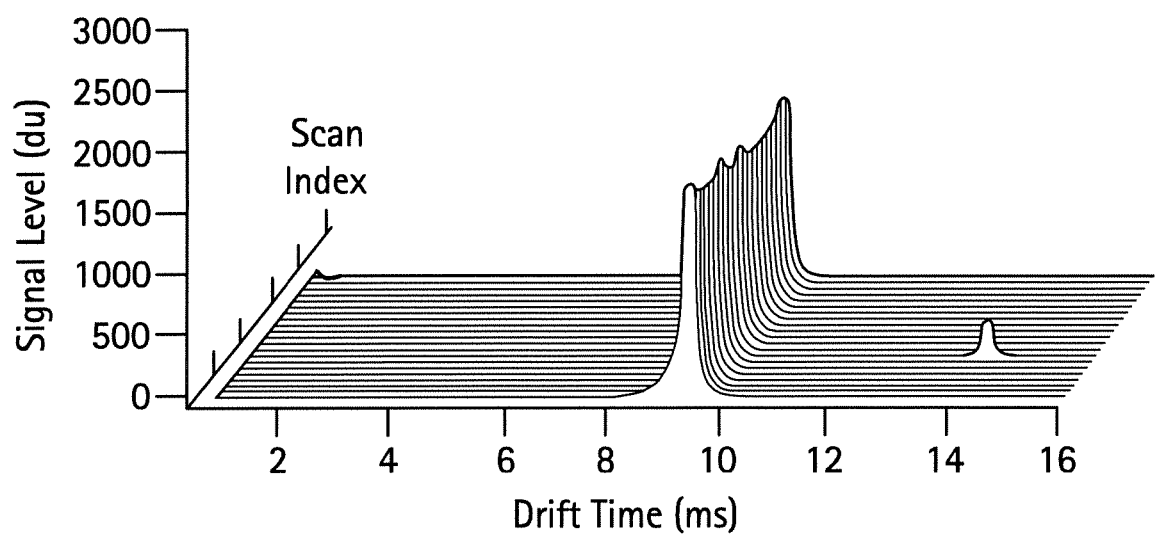
FIG. 2 is a graphical illustration of an exemplary three dimensional (3-D) plasmagram.

The 2-D plasmagram is a representation of one drift time scan by the IMS. However, during the testing of a sample, a number (n) of scans are conducted (e.g., at a rate of about 15 per second) to evaluate the effects of extended ionization on the sample. After the scans have been conducted, the data can be used to construct a 3-D plasmagram having drift time on the X-axis, signal level on the Y-axis and scan index (i.e., a sequential listing of individual scans) or time (e.g., calculated from the number of scans taken at a known rate) on the Z-axis, such as the exemplary 3-D plasmagram illustrated in FIG. 2.

Figure 3:
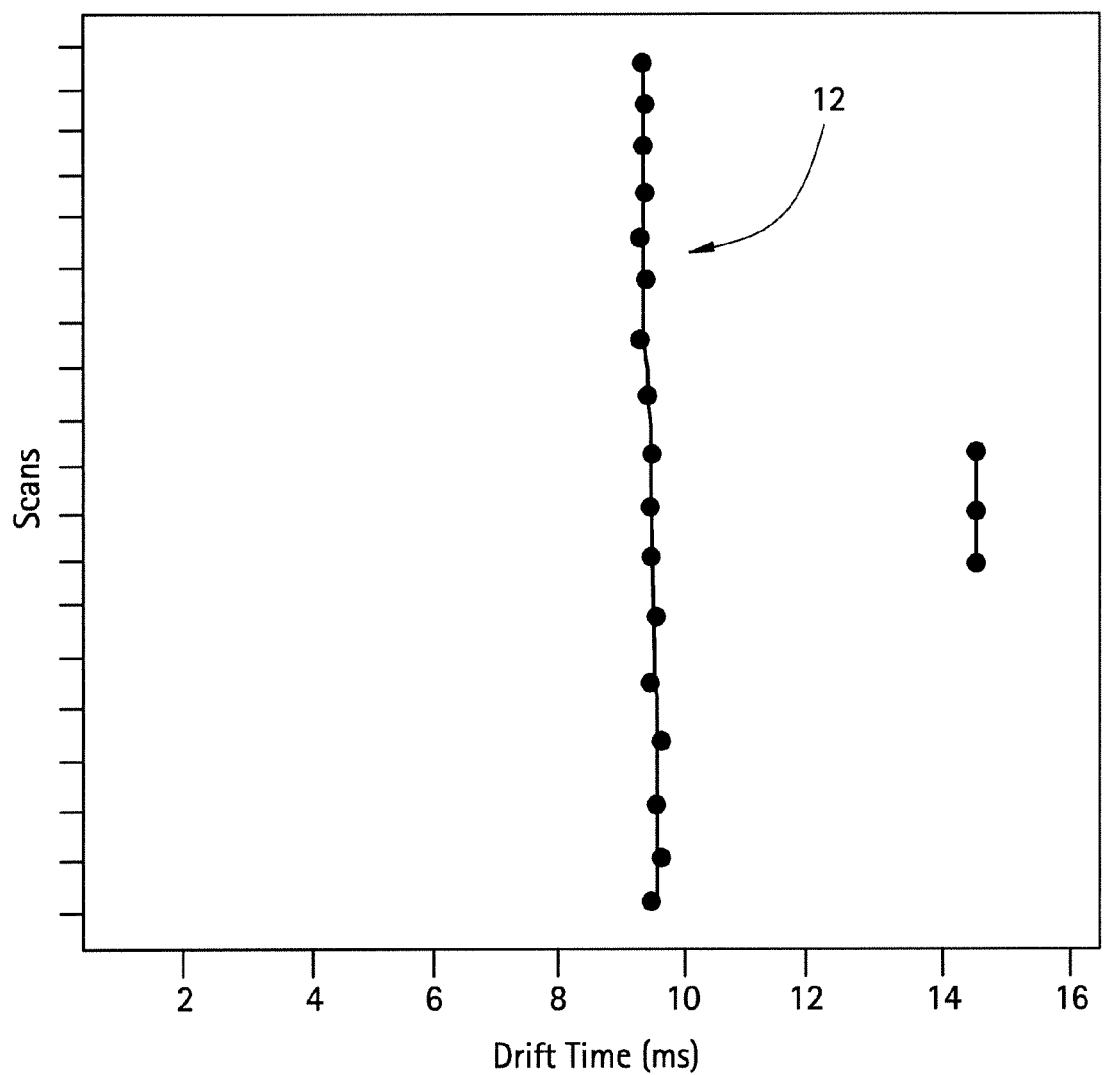
FIG. 3 is a 2-D graph having drift time on the X-axis and scan index on the Y-axis.

Once the data for a 3-D plasmagram have been collected they can be used to generate a two-dimensional graph called an intensity map, which presents drift time on the X-axis and scan index (or sample time) on the Y-axis, as illustrated in FIG. 3. On the graph the ionic signature of the substance is presented. The ionic signature comprises multiple ion lines that are formed by linking the maximum signal levels of a number (n) of sequential scans (or scans that are in close proximity) that are deemed comparable (e.g., comparable in drift time and/or in signal level). The line formation process can be enabled using any method of data analysis, algorithm, and so forth. For example, in one embodiment an ion line can be formed that comprises 45 sequential scans, wherein each sequential scan has a signal strength that is within 5% of the prior scan and has a drift time that is within 0.01 ms of the prior scan.

Once the intensity map is constructed, the ionic signature exhibited will differ between substances, and is thusly employed for identifying substances utilizing various methods, such as comparing an unknown ionic signature to a database of known ionic signatures. Optionally, intensity maps can present the signal levels of the drift time scans (e.g., the 2-D Plasmagram scans) using ion line colorations or other indicators (e.g., the color light blue can represent peak heights of 900 to 999 du's, dark blue can represent peak heights from 1,000 to 1,099 du's, and so forth).

Figure 4:
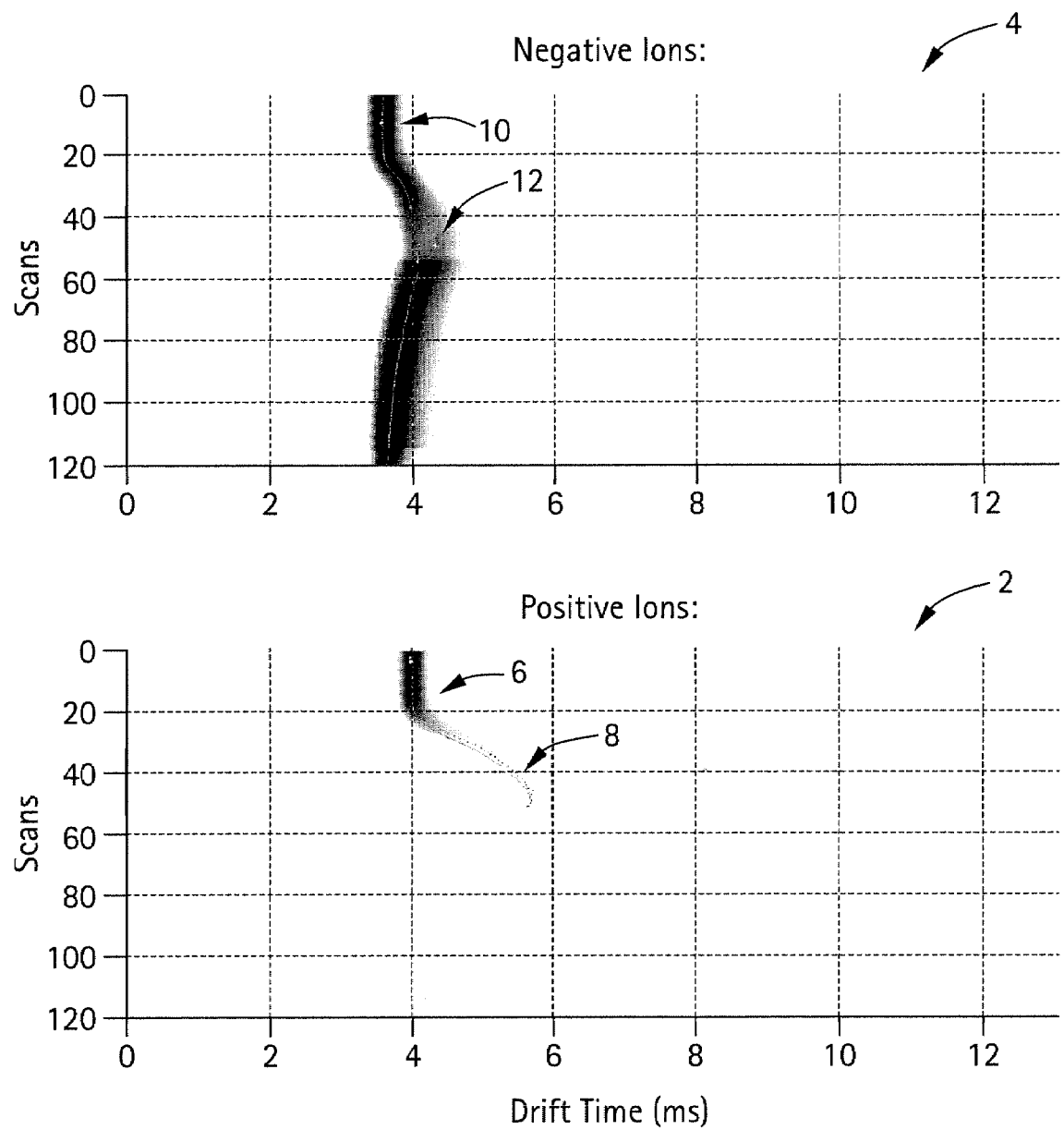
FIG. 4 is an intensity map illustrating a non-linear ion response.

As discussed, many substances generate linear ion lines, such as those illustrated in FIG. 3, which generally do not exhibit a slope with respect to sequential scans. However, some substances, such as those employed as taggants in explosives, exhibit curved or sloped ion lines that can be concentration dependent. For example, referring now to FIG. 4, an exemplary positive ion map 2 and negative ion map 4 are illustrated that comprise non-linear ionic signatures. Upon closer evaluation of the positive ion map 2, a positive ion line 6 originates at a drift time of about 0.40 milliseconds (ms), remains at this value for a number of scans, then begins to increase until it reaches a maximum drift time 8 of about 5.6 ms. Similarly, the negative ion map 4 exhibits a negative ion line 10 that originates at a drift time of about 3.5 ms that remains constant for several scans, then begins to increase, and reaches a maximum drift time 12 of about 4.5 ms.

The curved portions of the ion lines (e.g., positive ion line 6 and negative ion line 10) are indicative of the response exhibited by a target substance, wherein the drift time increases after a number of scans to a higher drift time.

One method of identifying contraband substances is to evaluate the positive and negative ion lines for drift time deviations and compare the lines for characteristics that are exhibited by contraband substances. This method is referred to as the Curvature Comparison Method (CCM).

The first step of the CCM method is to generate a positive ion map 2 for a sample of interest. The map can be constructed via any ion mobility apparatus or system that is capable of generating positive and negative ion drift time and peak intensity data over a plurality scans and converting the data into an intensity map. For example, one such apparatus that can be employed is the Itemiser DX Trace Detection System, commercially available from GE Security, Bradenton, Fla.

Once the positive ion map 2 (See FIG. 4) has been generated, the ionic signature (e.g., all of the positive ion line 6) is evaluated for curvatures. The evaluation is conducted by comparing the curvature of the ion lines to the expected system variance, if the curvature of the ion line is greater than the expected system variance, the line can be the result of a contraband substance and the CCM method proceeds. If the curvature of the ion line is not greater than the systems variance, the CCM method will deem the substance not to be a contraband substance.

The system variance can be a predefined value that is programmed into the IMS's operating system or hardware during manufacture, a value that is accessed or loaded by the IMS's operating system during each test or calculation, a value that is the result of the testing conducted, and so forth, as well as combinations of the aforementioned.

The specific method for evaluating if a curvature or slope is present within the positive ion map 2 can be any method that can identify a curvature with accuracy greater than or equal to about 70%, or even greater than or equal to about 80%, or even more specifically greater than or equal to about 90%. The specific method is chosen with respect to the number of scans, system variance, and other testing and data variables. One such analytical method that can be employed, e.g., which can be chosen when sample sizes are about 100 scans, utilizes the calculation of a statistic for comparison (Z), using the formula illustrated below.

$$Z = \frac{s - \sigma_{mzZ}}{\left(\sigma_m / \sqrt{2n}\right)} \quad (I)$$

Wherein:
Z=Statistic for Comparison
s=Standard Deviation Calculated from Drift Times of Line Data
$\sigma_m$=Hypothesized Standard Deviation (Standard Deviation of the System Measurement Noise)
n=Number of Scans The statistic for comparison (Z) can be compared to a normal curve standard ($Z_\alpha$) to determine if a null hypothesis or an alternate hypothesis will be chosen. The null hypothesis ($H_o$) represents that, with respect to time, the standard deviation s (standard deviation calculated from drift times of line data) of the ion line is equal to the hypothesized standard deviation $\sigma_m$ (standard deviation of the system measurement noise) while the alternate hypothesis ($H_a$) represents that the standard deviation s is greater than the hypothesized standard deviation $\sigma_m$.

The normal curve standard ($Z_\alpha$) for a one-tailed normal distribution can be chosen to provide a desired confidence that the correct hypothesis is chosen. For example, for 95% confidence ($\alpha=0.05$) that the correct hypothesis was chosen, a normal curve standard of 1.645 is chosen; if 99% confidence (e.g., $\alpha=0.01$) is desired, a curve standard of 2.33 can be chosen. Using the 99% confidence interval, if Z is less than $Z_\alpha$, the null hypothesis ($H_o$) is selected, which implies the curvature of an ion line being evaluated is not indicative of a contraband substance. If Z is equal to or greater than $Z_\alpha$, the alternative hypothesis ($H_a$) is selected, which implies the curvature is indicative of a contraband substance.

If the null hypothesis is chosen, the CCM method is abandoned and the IMS can continue to an alternative action. If the alternative hypothesis is chosen, the CCM method can continue to additional steps to ensure the positive ion line 6 is not a false positive (e.g., a false alarm). It is to be apparent that the positive ion map 2 can comprise an ionic signature comprising more than one suspect positive ion line. In such cases, the CCM method is employed to evaluate each suspect positive ion line 6.

Several sub-tests can be conduced to ensure the positive ion line 6 is not a false positive. The first sub-test evaluates if the maximum drift time 8 of the positive ion lines 6 occurs prior to a specific acceptable scan index value. To be more specific, many contraband substances exhibit a maximum drift time 8 in less than or equal to 5 seconds. For example, a maximum drift time 8 is attained prior to the $70^{th}$ scan, which corresponds to about 4.66 seconds wherein each scan is conducted at a rate of about $\frac{1}{15}$ second. Not to be limited by theory, this characteristic is believed to be due to the volatility of these chemicals, which undergo many chemical reactions during extended ionization times. It is to be apparent however that the specific acceptable scan index value (or sample time value that can be calculated from the scan index) can be altered based on variables associated with the sample, the apparatus, the testing conditions, the carrier gas, and so forth.

If the maximum drift time 8 for the positive ion line 6 is greater than the specific acceptable scan index value (e.g., 70 scans), the sample is considered not to be a contraband substance and the CCM method is abandoned. If a positive ion line 6 exhibits a maximum drift time 8 that is equal to or less than the specific acceptable scan index value, the CCM method advances to conduct additional false positive tests.

The second false positive sub-test compares the maximum drift time 8 on the positive ion line(s) 6 to a maximum drift time 12 of the negative ion line(s) 10. To be more specific, it has been discovered that the scan index of the maximum drift time 8 on the positive ion map 2 will roughly correspond to the scan index of the maximum drift time 12 of the negative ion map 4 if the sample substance is a contraband substance.

To conduct the analysis, a negative ion map 4 is constructed if not already done so. Thereafter, the scan index of the maximum drift time 8 on the positive ion map 2 is utilized to construct an acceptance window. The scan index of the maximum drift time 12 on the negative ion map 4 can then be compared to the acceptance window. If the maximum drift time 12 from the negative ion map 4 is within the acceptance window calculated around the maximum drift time 8 from the positive ion map 2, the suspect substance will be considered a contraband substance and the CCM method will continue. If this is not the case, the substance will be determined to not be a contraband substance.

The acceptance window allows for variations in testing, map construction, data interpretation, and so forth, such that if the scan index of the maximum drift time 12 of the negative map 4 is not exactly similar to the scan index of the maximum drift time 8 of the positive map 2, the sample will not be deemed a non-contraband. The acceptance window is constructed around the scan index of the maximum drift time 8 of the positive ion map 2 using it as a median from which upper and lower acceptable range values are calculated. To be more specific, the upper acceptable range value is calculated by adding an upper scan variation number thereto, and the lower acceptable range value is calculated by subtracting a lower scan variation number therefrom.

For example, in one embodiment an Itemiser DX Trace Detection System, commercially available from GE Security, Bradenton, Fla. is employed to test a contraband sample. For this apparatus, the acceptance window is calculated using an upper acceptable range value of 12 scans and a lower acceptable range value of 12 scans, which was determined based on the variance of the testing apparatus. Therefore, if a sample produced a positive ion map 2 having a maximum drift time 8 at a scan index of 45 (i.e., the $45^{th}$ scan conducted), the acceptance widow would be equal to about 33 to about 57 scans. Thus, if a substance produced a negative map 4 that included a line having a scan index of the maximum drift time 12 of about 52, which is within the acceptance window, the sample would be deemed a contraband substance and the CCM method would continue. However, if the sample produced a negative ion map 4 that included a line having a scan index of about 76 at the maximum drift time 12, this would not lie within the acceptance window and the CCM would be abandoned.

Substances that produce non-linear drift time responses may also exhibit a concentration dependency with respect to their maximum drift time. To be more specific, the maximum drift time can increase with an increase in substance concentration. In addition, the scan time at which the maximum drift time occurs also increases with increased concentration. This concentration-dependent characteristic may lead to an ion line that does not show a maximum drift time but, instead, presents a monotonically increasing drift time. This effect may also occur if the ion map scan sequence is terminated before the concentration-dependent drift time maximum value is observed. Therefore, in cases wherein the positive ion lines exhibit a maximum drift time 8 that is greater than a scan index of 48, the upper acceptable range value is increased to provide a greater acceptable range. Specifically, with regard to the example above for the Itemiser DX Trace Detection System, the upper acceptable range value is increased to 22 for the Itemiser DX Trace Detection System. It is to be apparent however that the upper and lower acceptable range values are dependent upon testing, sample, and other variables.

In cases wherein the scan index of the maximum drift time 12 on the negative ion map 4 occurs early in the scanning process (e.g., within the first five scans) the variation between the positive and negative ion maps can be greater than when this does not occur. In such cases, the upper acceptable range value is increased to provide a greater acceptable range. Specifically, with regard to the example above for the Itemiser DX Trace Detection System, the upper acceptable range value is increased to 22 for the Itemiser DX Trace Detection System.

Alternatively, or in conjunction with the above tests, a ratio test can be employed to determine if the test sample is a contraband substance or a false positive result. The ratio test comprises calculating the ratio of the maximum drift time 8 shown by the positive ion map 2 to the maximum drift time 12 shown by the negative ion map 4. If the ratio is within an predetermined range, such as about 0.5 to about 2.0, or, more specifically, about 1.0 to about 1.75, or even more specifically, about 1.19 to about 1.58, the sample can be considered a contraband substance and not a false positive.

Another test serves to eliminate false alarms by excluding any ion lines that present a maximum drift time in excess of a specified limit, such as 11 ms. If the positive or negative ion line presents a maximum drift time less than this limit, it is considered a contraband substance and not a false positive (e.g., a false alarm).

If the test sample has not been ruled out as a false positive by the comparative methods above, a final, signal level threshold test of the negative ion line 10 can be conducted. To be more specific, if the signal level or signal intensity of the negative line at the scan containing maximum drift time 12 is greater than or equal to a specific signal level, such as 2,000 du, the sample is deemed a contraband substance and the system declares detection of the contraband.

Figure 5:
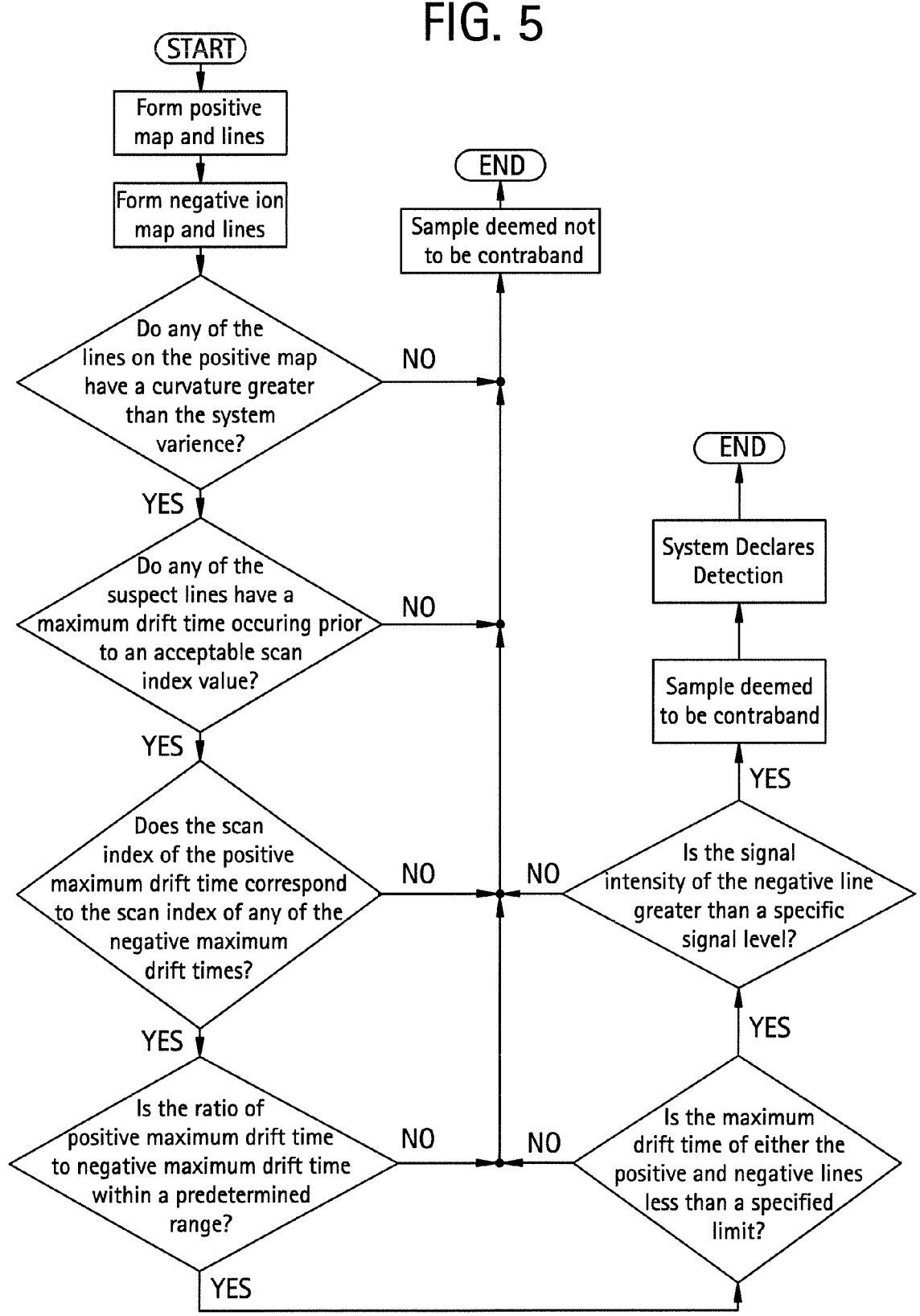
FIG. 5 is an exemplary flow chart of the Curvature Comparison Method (CCM).

As described, the Curvature Comparison Method (CCM) initiates with the evaluation of the positive ion line 6. However, it is to be apparent that the CCM method can also be conducted by first evaluating the negative ion line and comparing positive ion lines to validate a detection and eliminate false positives. An exemplary flow chart illustrating the Curvature Comparison Method (CCM) is illustrated in FIG. 5.

A second method for analyzing ion mobility data is to detect the presence of contraband substances is the non-flat detection method. The non-flat detection method numerically compares the positive ion line's data to the numerical data of the negative ion line 10 for non-flatness, which can be employed to detect the characteristic non-linear curves in drift time exhibited by contraband substances.

During the testing of a sample, the data gathered could be parsed, manipulated, and/or stored in any manner that provides ease of accessibility and/or data management. One such method of storing data is in the form of arrays. Hence, the non-flat detection method comprises creating data array(s) for sample time data and second array(s) for drift time data for each scan. Optionally, additional arrays can be created for data such as signal level data, adjusted amplitude data, and so forth.

After the sample time and drift time arrays have been created, the drift time values are analyzed with respect to sample time so that ion lines can be identified (e.g., positive ion lines 6 and/or negative ion line 10). In addition, start and stop data for the lines are detected and imported into four additional arrays: the first comprises positive start data, the second comprises positive stop data, the third comprises negative start data, and the fourth comprises negative stop data.

The ion lines identified are then individually evaluated for non-flatness. To calculate non-flatness for a line, the average drift time is first calculated using equation (II) below. Once the average drift time has been calculated, the non-flatness of each ion lines is calculated using equation (III) below.

$$avg = \frac{\sum_{i=Start}^{Stop} td(i)}{(Stop - Start + 1)} \quad (II)$$

$$\text{Non-Flatness} = \frac{\sum_{i=Start}^{Stop} td(i) - avg}{avg * (Stop - Start)} \quad (III)$$

wherin:
avg=Average Drift Time
td(i)=Drift time of the $i^{th}$ scan index
Start=Scan Index of the first data point of the line
Stop=Scan Index of the last data point of the line
n=Number of scans of the line Once the non-flatness of each line has been calculated, the positive ion line 6 and the negative ion line 10 that exhibit the largest non-flatness values are identified. These two lines are referred to as the most non-flat lines.

The first detection confirmation test is to evaluate the pair of most non-flat lines relative to conditions exhibited by contraband substances. A first evaluation of the non-flatness can be conducted to determine if either the most non-flat positive ion line (e.g., positive ion line 6) or the most non-flat negative ion line (e.g., negative ion line 10) comprise a non-flatness that is equal to or greater than a minimum non-flatness value (e.g., 0.085 for the Itemiser DX Trace Detection System). If this is true, the sample is considered to comprise a contraband substance. However, if this is not true, a second and third detection confirmation tests are conducted.

The second detection confirmation test evaluates if the non-flatness of the most non-flat positive line (e.g., positive ion line 6) is greater than or equal to about 0.01, or more specifically about 0.02, or, more specifically, about 0.0225, and comprises a maximum drift time that is equal to or greater than about 2 ms, or more specifically, about 4 ms, or, even more specifically, about 4.65 ms, at a scan time that is greater than or equal to about 2 seconds, or, more specifically, about 4 seconds, and, even more specifically, about 4.83 seconds. If this is true, the sample is considered to comprise a contraband substance. If this is not true, the non-flatness detection method advances to the third detection confirmation test.

The third detection confirmation test evaluates if the non-flatness of the most non-flat negative ion line 10 is greater than or equal to about 0.01, or more specifically about 0.02, or, more specifically, about 0.0225, and comprises a maximum drift time that is equal to or greater than about 2 ms, or more specifically, about 4 ms, or, even more specifically, about 4.65 ms, at a scan time that is greater than or equal to about 2 seconds, or, more specifically, about 4 seconds, and, even more specifically, about 4.83 seconds. If this is false, the sample is considered not to comprise a contraband substance. If this is true, the substance tested is considered a contraband substance.

If either of the first, second or third detection confirmation tests are true, three additional false positive tests are conducted (i.e., the fourth, fifth, and sixth false positive tests) to reduce the occurrence of a false positive assumption.

The fourth false positive test evaluates if the non-flatness of the most non-flat positive ion line (e.g., positive ion line 6) is less than or equal to about 0.001, or, more specifically, about 0.0003. If this is true, the substance is considered not to be a contraband substance. If this is not true, the fifth test is initiated.

The fifth false positive test evaluates if the line length (e.g., the number of data points within the most non-flat positive ion line (e.g., positive ion line 6)) comprises about 50 to about 55 data points and if the maximum drift time 8 at a permissible range, e.g., about 3 to about 5 ms, or more specifically, about 4.0 to about 4.1 ms. If this is true, the substance is considered not to be a contraband substance. If this is not true, the sixth test is initiated.

The sixth false positive test evaluates if the most non-flat positive ion line (e.g., positive ion line 6) is about 50 to about 55 data points and if the maximum drift time 8 occurs at a permissible range, e.g., about 9 to about 14 ms, or more specifically, about 11 and about 12 ms. If this is true, the sample is deemed to not comprise a contraband substance. If this is not true, the sample is considered to comprise a contraband substance.

The third method of analyzing ion mobility spectrometry data for the detection of contraband substances is the signature detection method. The signature detection method comprises a pre-qualification step, signature matching step and a post qualification step.

Figure 6:
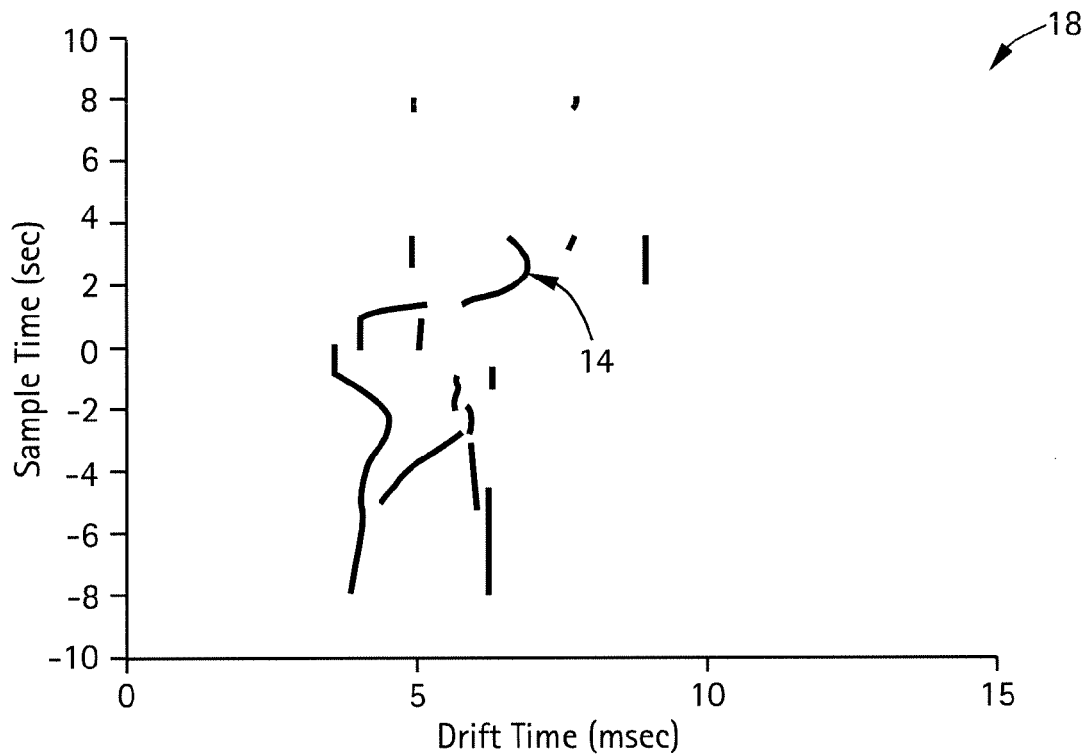
FIG. 6 is a composite line set comprising a composite ion line.

The first step of the signature detection method is to generate a positive ion map 2 and a negative ion map 4 for a sample of interest. Once the maps have been created they are combined to form a composite line set. This composite line set is built by inverting the order of the positive ion scans (increasing scan index runs up the vertical axis as shown in FIG. 6) and stacking the positive ion scans above the negative ion map 4. Furthermore, the negative ion map 4 scan index is changed to a negative integer. As shown in FIG. 6, the composite line set 18 can be represented as a two-dimensional graph having drift time (ms) on the X-axis and sample time (sec) on the Y-axis. Once the scan index values are reassigned, the scan index values for the positive and negative ion lines are converted to time using the known scan rate of the apparatus (e.g., 15 scans/sec) to allow matching in the event scan rate is varied. The inverted positive ion lines 6 and the negative ion lines 10 are then jointly displayed on a composite line set 18 as composite ion lines 14.

The pre-qualification step evaluates if the ion lines in the composite line set 18 exhibit the characteristic drift time curvature that is produced by contraband substances (e.g., a composite ion line 14). This is achieved by evaluating the lines that lie within the scan time range of about 0.5 to about 5 seconds, or, more specifically, about 1 to about 4 seconds, or, even more specifically, about 1.2 to about 3.5 seconds. If any of the lines within this time range exhibit a drift time variation equal to or greater than about 0.1 ms, or, more specifically, equal to or greater than about 0.2 ms, or, even more specifically, equal to or greater than about 0.3 ms, the signature detection method will continue to the signature matching step. If the lines do not comprise a drift time variation that satisfies the above conditions the sample is deemed not to be a contraband substance. Referring again to FIG. 6, it can be seen on the composite line set 18 that the exemplary composite ion lines 14 satisfies the pre-qualification test as the composite ion line 14 varies in drift time greater than or equal to about 0.4 ms in a window of about 1.2 to about 3.5 seconds.

If an ion line is detected that satisfies the conditions of the pre-qualification step, the signature matching step is initiated to identify a known ion line that exhibits the closest resemblance to the suspect ion lines. To achieve this, a library of ion lines is accessible by the apparatus (e.g., a database) that can be compared to the ion lines produced by the suspect sample.

The library comprises a variety of contraband substances at varying concentrations. For example, an array can be constructed comprising trinitrotoluene (TNT), hexanitrobenzene (HNB), octanitrocubane, nitrogen triiodide, 1,3,5-Triazido-2,4,6-trinitrobenzene, ammonium nitrate, and so forth, tested in 1 microgram (µg) increments from about 1 µg to about 50 µg for comparison to the suspect ion lines. The data within the library can be parsed in any manner to enable efficient comparison to the suspect ion lines. In one embodiment an array can be constructed wherein each column comprises the maximum drift time data and position data of the maximum drift time (e.g., converted from scan index to sample time in seconds) for individual ion lines, wherein the total entries within the column represent the length of the line.

The suspect ion lines are compared to each ion line within the library. During the comparison, each drift time data point (hereinafter referred to as a data point) for each line within the library is compared to the data points of the suspect ion lines with respect to the scan time of the data points. It is noted that the suspect ion data can be multiple lines having gaps therebetween. From this comparison a match score is calculated with respect to the number of data points of the suspect ion lines that are considered equivalent to a data point within the known ion line.

Data points are considered equivalent if the drift time data points are within a Gaussian function applied to each drift time data point of the library ion lines. For example, a known ion line accessed from the library comprises a maximum drift time of 7.5 ms at 2 seconds sample time and a suspect ion line comprises a maximum drift time of 7.2 ms at 2 seconds sample time. Upon review, the data points are not equal. However, employing a Gaussian function with a sigma squared value of about 0.2 would produce a normal distribution of acceptable values centered about the 7.5 ms median of the known ion line having an acceptance range of about 6.9 ms to about 8.1 ms, as approximated by three standard deviations above and below the median of 7.5 ms. In this example, the data points are considered equivalent and therefore the overall match score of the line is increased.

The match score for each data point can be a fixed value or variable based upon the deviation between the known maximum drift time value and the suspect ion line's maximum drift time value. An example wherein the amount the match score is increased is fixed for each acceptable data point would be if the suspect ion line's maximum drift time value at a specific sample time is within the allowable range created by the Gaussian distribution and the match score increases by a fixed amount. An example wherein the amount the match score is increased by a variable amount would be if the match score increased as a function of the position of the suspect ion line's maximum drift time value in relation to the maximum drift time of the known sample within the Gaussian distribution. Stated another way, as the suspect line's maximum drift time data point deviates from the median, the match score will decrease by a variable amount. In one embodiment for example, the match score can be related to the number of standard deviations it lies away from the median, such as an algorithm created to assign a full incremental increase in the match score for a data point that lies within one standard deviation from the median, assigns two-thirds of the incremental amount to increase the match score for data points that lie within two standard deviations but greater than one standard deviation from the median, and one-third of the incremental amount to increase the match score for data points that lie within three standard deviations but greater than two standard deviation from the median.

The match score can be any number that is a generated with respect to the data point equivalency analysis described above. In one embodiment, the match score can be the total sample time that the suspect ion line matches a known ion line from the library (e.g., each data point that is found equivalent can represent a length of time, the summation of the data points multiplied by the increment of time assigned to each point yields the total time). In another embodiment each data point that is found equivalent can be considered a match score point.

A match score is calculated for each known ion line within the library. The ion line exhibiting the highest match score, which is referred to as the best-fit ion line, is compared to a minimum acceptable match score value. If the suspect ion line exhibits a match score that is equal to or greater than the minimum acceptable match score value the signature detection method will advance. If the suspect ion line does not exhibit a match score that is less than the minimum acceptable match score value the sample is deemed not to comprise a contraband substance and the signature detection method is halted. For example, in one embodiment a minimum acceptable match score of 5.0 seconds can be employed for a system that employs match score as a function of sample time. In this example, if a suspect ion line produces a match score that is equal to or greater than 5.0 seconds the signature detection method will advance. If the suspect ion line exhibits a match score that is less than 5.0 seconds, the sample will be deemed not to comprise a contraband substance and the signature detection method will be halted.

Figure 7:
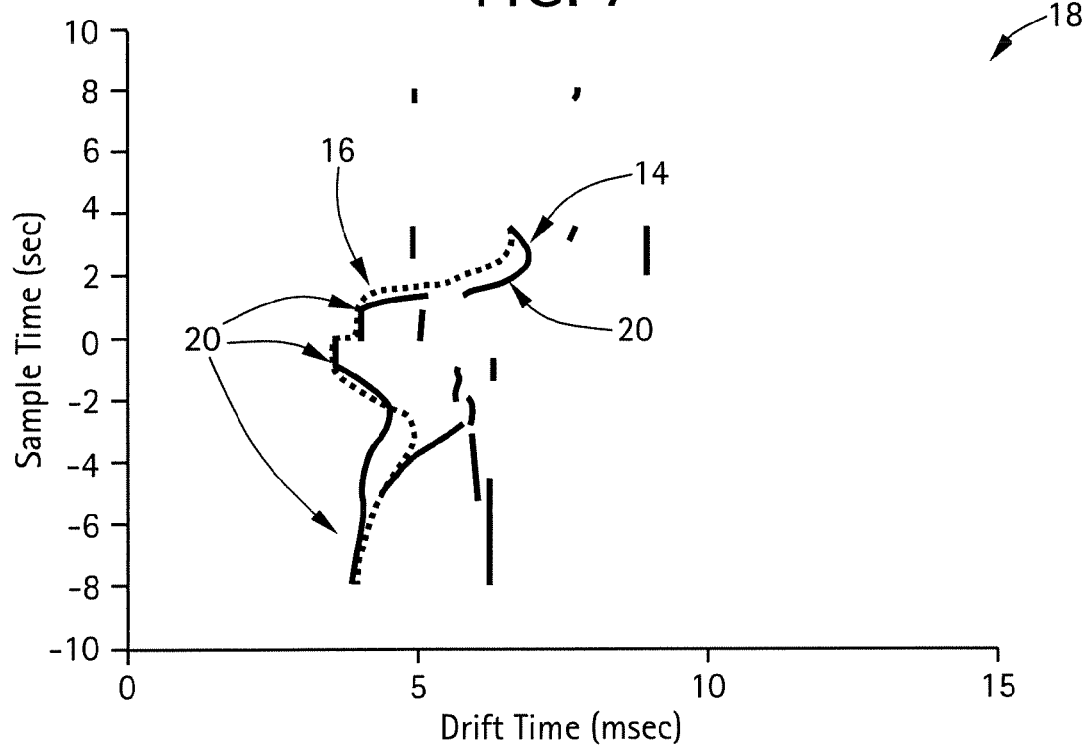
FIG. 7 is a composite line set having suspect ion lines that comprises a composite ion line.

Referring now to FIG. 7, a composite line set 18 is illustrated having suspect ion line segments 20 that comprise a composite ion line 14. Also illustrated is a best-fit ion line 16. The best-fit ion line 16 is a representation of the ion line that exhibits the highest match score.

To mitigate false positives using the signature detection method, a post qualification step can be performed. The post qualification step evaluates if the suspect ion line's data comprise enough data points to construct a suspect ion line(s) 20 within a sample time window of about 0.5 to about 5 seconds, or, more specifically, about 1 to about 4 seconds, or, even more specifically, about 1.2 to about 3.5 seconds on the composite line set 18, and if the constructed suspect ion line(s) 20 is within an acceptable drift time range (e.g., about +/−4 ms, or, more specifically, +/−3 ms, or even more specifically, +/−2 ms) centered about the best-fit ion line 16. If this is satisfied, the suspect ion line(s) 20 is considered to comprise a contraband substance. If this is not satisfied, the suspect ion line(s) 20 is not considered to be a contraband substance. Stated another way, for example, the post qualification test analyses if a suspect ion line(s) 20 exists within the sample time window of about 1.2 to about 3.5 seconds. A suspect ion line(s) 20 will only be constructed within this range if the suspect ion drift data comprise at least a minimum number of data points (e.g., 5 maximum drift time data points) at sequential scan indexes (or sample times, or scan indexes that are close in proximity to one another as decided by a line formation algorithm) within the sample time window of 1.2 and 3.5 seconds that meet the requirements of the line formation algorithm so that a line segment is constructed. If the suspect ion data support the construction of a line within the sample time window of 1.2 and 3.5 seconds, if each data point (or a majority of the data points, or even a number of the data points) that form the suspect ion line(s) 20 is within a drift time range of +/−3.0 ms from the corresponding data point of the best-fit ion line's data point, then the suspect ion line(s) 20 is considered to comprise a contraband substance.

Figure 8:
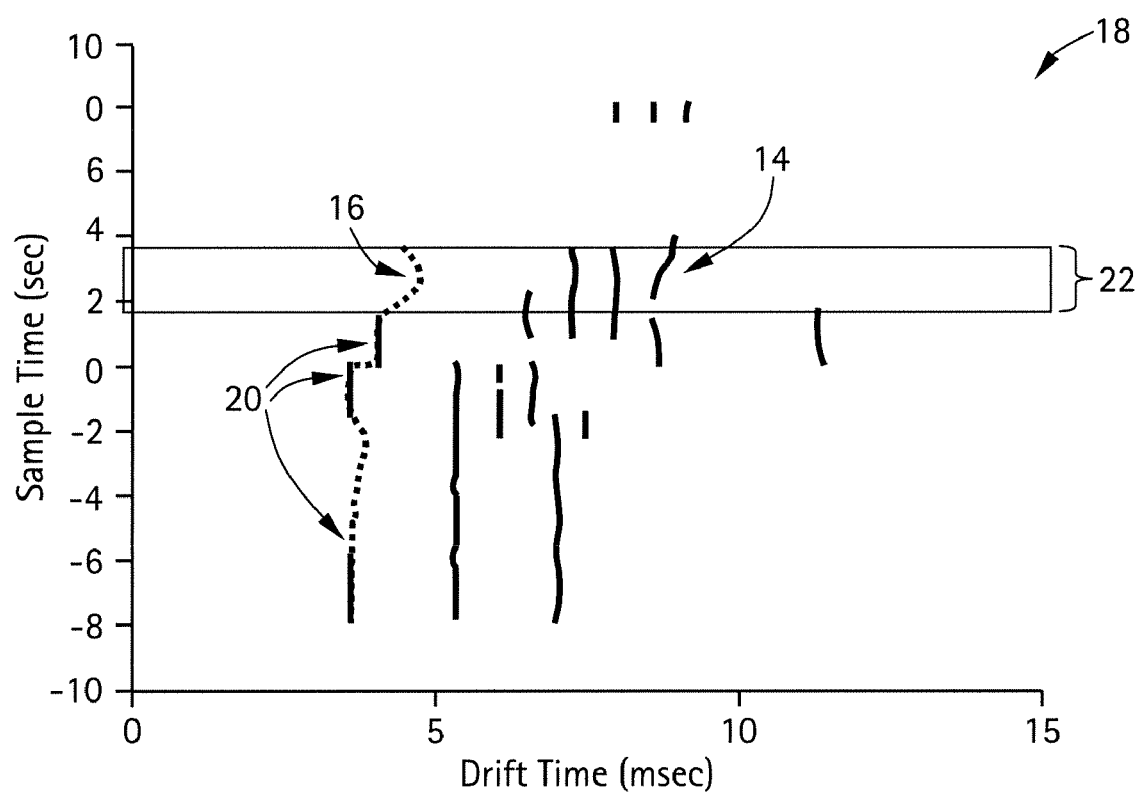
FIG. 8 is a composite line set comprising a composite line, a suspect ion line(s) and a best-fit ion line.

For example, refer now to FIG. 8, wherein a composite line set 18 comprises a composite line 14, a suspect ion line(s) 20 and a best-fit ion line 16 (e.g., a known ion line from a library). The first step of the signature detection method determined that composite line 14 exhibited a deviation in drift time that was equal to or greater than an exemplary minimum value of 0.3 ms within the sample time window 22 of about 1.2 to about 3.5 seconds due to composite line 14. The second step of the signature detection method determined a best-fit curve 16 and the suspect ion line(s) 20 comprised a match score that was equal to or greater than 5.0 seconds of equivalent data points, wherein in this example the match score was calculated by converting the number of consecutive data points within the sample time window that were considered equivalent to the best-fit ion line (the known ion line). However, the suspect ion line(s) 20 does not comprise ion lines that are within +/− about 3 ms from the best-fit ion line 16. Therefore, the suspect ion line(s) 20 is deemed to not comprise a contraband substance.

The disclosed methods can be embodied in the form of computer or controller implemented processes and apparatuses for practicing those processes. These methods can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the method. The methods may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the method. When implemented on a general-purpose microprocessor, the computer program code segments configure the microprocessor to create specific logic circuits.

Unless defined otherwise, technical and scientific terms used herein have the same meaning as is commonly understood by one of skill in the art to which this invention belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the colorant(s) includes one or more colorants). Furthermore, as used herein, "combination" is inclusive of blends, mixtures, alloys, reaction products, and the like.

Further, several designs of ion mobility spectrometers are disclosed herein with references to individual figures. One of skill in the art will easily recognize that many of the components of each of the embodiments are similar to or identical to each other. These various components can be added or omitted based on various design choices. As such, various elements and/or features can be introduced in a given figure with the understanding that the ion mobility spectrometer can be modified as taught herein to include features illustrated in other embodiments. Each of these elements is first introduced in the discussion of a given figure, but is not repeated for each embodiment. Rather, distinct structure is discussed relative to each figure/embodiment.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for analyzing ion mobility spectrometry data, comprising: conducting a number of ion mobility scans on a sample; generating an ion map comprising a first ion line; comparing the first ion line to a standard deviation, wherein the standard deviation is calculated from a system measurement noise, said comparing comprising; identifying a first maximum drift time and a corresponding first scan index for the first ion line; calculating the standard deviation ($s_m$) of the first ion line; calculating a statistic for comparison (Z) using the formula:

$$Z = \frac{s - \sigma_m}{\left(\sigma_m / \sqrt{2n}\right)},$$

wherein s represents system measurement noise standard deviation; identifying a normal curve standard ($Z_a$); comparing the statistic for comparison (Z) to the normal curve standard ($Z_a$); and, determining if the sample is a contraband substance.

2. The method of claim 1, further comprising determining if the first scan index is less than or equal to about 70.

3. The method of claim 1, further comprising determining if the first maximum drift time corresponds to a sample time that is less than or equal to about 5 seconds.

4. The method of claim 1, further comprising determining if the first maximum drift time is greater than or equal about 11 ms.

5. The method of claim 1, further comprising: generating a second ion map comprising a second ion line; identifying a second maximum drift time and a corresponding second scan index for the second ion line; generating an acceptance window that is centered about the first scan index; and, determining if the second scan index is within the acceptance window.

6. The method of claim 5, further comprising:
calculating a drift ratio of the first maximum drift time to second maximum drift time, wherein the drift ratio is a value; and,
determining if the value is about 0.5 to about 2.0.

7. The method of claim 6, wherein the value is about 1.0 to about 1.75.

8. The method of claim 7, wherein the value is about 1.19 to about 1.58.

9. The method of claim 1, further comprising evaluating if a maximum signal level amplitude at the first scan index is greater than or equal to a specific signal level.

10. The method of claim 9, wherein the specific signal level is about 2,000 du.

11. A method for analyzing ion mobility spectrometry data, comprising:
conducting a number (n) of ion mobility scans on a sample;
generating a first data array comprising a plurality of scan times;
generating a second data array comprising a plurality of drift times (td);
identifying an ion line using the first data array and second data array, wherein the ion line comprises a line length, a start point (start) and a stop point (stop);
calculating an average drift time (avg) for the ion line using the formula:

$$avg = \frac{\sum_{i=Start}^{Stop} td(i)}{(Stop - Start + 1)};$$

calculating a non-flatness value (Non-Flatness) using the formula:

$$\text{Non-Flatness} = \frac{\sum_{i=Start}^{Stop} td(i) - avg}{avg * (Stop - Start)}; \text{ and,}$$

determining if the sample is a contraband substance.

12. The method of claim 11, further comprising determining if the non-flatness value is greater than or equal to about 0.085.

13. The method of claim 11, further comprising:
identifying a maximum drift time; and,
determining if the non-flatness value is greater than or equal to about 0.01 and if the maximum drift time is equal to or greater than about 2 ms at a scan time that is greater than or equal to about 2 seconds.

14. The method of claim 13, wherein the non-flatness value is greater than or equal to about 0.02, wherein the maximum drift time is equal to or greater than about 4 ms, and the scan time is greater than or equal to about 4 seconds.

15. The method of claim 14, wherein the non-flatness value is greater than or equal to about 0.0225, wherein the maximum drift time is equal to or greater than about 4.65 ms, and the scan time is greater than or equal to about 4.85 seconds.

16. The method of claim 11, further comprising determining if the non-flatness value is less than or equal to about 0.001.

17. The method of claim 11, wherein the non-flatness value is less than or equal to about 0.0003.

18. The method of claim 11, further comprising:
identifying a maximum drift time; and,
determining if the ion line comprises a line length comprising about 50 to about 55 data points and comprises a maximum drift time that is at a permissible range.

19. The method of claim 18, wherein the permissible range is about 3 to about 5 ms.

20. The method of claim 19, wherein the permissible range is about 4 to about 4.1 ms.

21. A method for analyzing ion mobility spectrometry data, comprising: conducting an ion mobility scan on a sample; constructing a composite line set comprising a composite ion line formed by data points; determining if the composite ion line exhibits a variation in drift time that is greater than or equal to a minimum value within a scan time range; comparing the composite ion line to a known ion line, wherein the known ion line comprises known data points; calculating a match score for the composite ion line; comparing the match score to a minimum acceptable match score; and determining if the sample is a contraband substance.

22. The method of claim 21 wherein the scan time range is about 0.5 seconds to about 5 seconds and the minimum value is 0.1 ms.

23. The method of claim 22 wherein the scan time range is about 1 seconds to about 4 seconds and the minimum value is 0.2 ms.

24. The method of claim 23 wherein the scan time range is about 1.2 seconds to about 3.5 seconds and the minimum value is 0.3 ms.

25. The method of claim 21, wherein the match score is calculated by determining the number of data points that are considered equivalent to the known data points within the scan time range.

26. The method of claim 25, wherein the number of data points that are considered equivalent is based on a proximity of the data point to the known data point, wherein the data point and the known data point are at an equivalent scan time.

27. The method of claim 26, wherein the proximity is determined using a Gaussian distribution.

28. The method of claim 21, further comprising: determining if the composite ion line comprises a portion that is within a sample time window; and,
determining if the portion is within a drift time range, wherein the drift time range is centered about a segment of the known ion line within the sample time window.

29. The method of claim 28 wherein the sample time window is about 0.5 to about 5 seconds and the drift time range is +/− about 4 ms.

30. The method of claim 29 wherein the sample time window is about 1 to about 4 seconds and the drift time range is +/− about 3 ms.

31. The method of claim 30 wherein the sample time window is about 1.2 to about 3.5 seconds and the drift time range is +/− about 2 ms.

* * * * *